US012716843B2

(12) United States Patent
Türschmann et al.

(10) Patent No.: US 12,716,843 B2
(45) Date of Patent: Aug. 25, 2026

(54) OPTOELECTRONIC CHIP

(71) Applicant: Bruker Optics GmbH & Co. KG, Ettlingen (DE)

(72) Inventors: Pierre Türschmann, Erlangen (DE); Daniel Böning, Erlangen (DE)

(73) Assignee: Bruker Optics GmbH & Co. KG, Ettlingen (DE)

( * ) Notice: Subject to any disclaimer, the term of this patent is extended or adjusted under 35 U.S.C. 154(b) by 218 days.

(21) Appl. No.: 18/270,163

(22) PCT Filed: Sep. 30, 2021

(86) PCT No.: PCT/EP2021/076981
§ 371 (c)(1),
(2) Date: Jun. 28, 2023

(87) PCT Pub. No.: WO2022/144102
PCT Pub. Date: Jul. 7, 2022

(65) Prior Publication Data
US 2024/0069317 A1 Feb. 29, 2024

(30) Foreign Application Priority Data

Dec. 29, 2020 (DE) ..................... 10 2020 135 024.4
May 11, 2021 (DE) ..................... 10 2021 112 251.1
May 11, 2021 (DE) ..................... 10 2021 112 256.2

(51) Int. Cl.
*G01N 21/64* (2006.01)
*G01N 33/557* (2006.01)
(Continued)

(52) U.S. Cl.
CPC ..... *G01N 21/6458* (2013.01); *G01N 21/6428* (2013.01); *G01N 21/648* (2013.01);
(Continued)

(58) Field of Classification Search
CPC ............ G01B 11/0675; G01B 2290/30; G01B 2290/70
See application file for complete search history.

(56) References Cited

U.S. PATENT DOCUMENTS 5,479,260 A 12/1995 Fattinger
5,653,008 A 8/1997 Sim et al.
(Continued)

FOREIGN PATENT DOCUMENTS

CN 102713578 A 10/2012
CN 103335993 A 10/2013
(Continued)

OTHER PUBLICATIONS

Agnarsson et al., Evanescent Light-Scattering Microscopy for Label-Free Interfacial Imaging: From Single Sub-100 nm Vesicles to Live Cells, Acs Nano., 9(12):11849-11862 (2015).
(Continued)

*Primary Examiner* — Van N Chow
(74) *Attorney, Agent, or Firm* — MARSHALL, GERSTEIN & BORUN LLP

(57) ABSTRACT

The present invention relates to an optoelectronic chip for receiving a sample for optical examination, having a carrier layer, a thin-film lightguide having an active region, in which the sample interacts with a guided mode of the thin-film lightguide, wherein at least one scattering structure is arranged in the active region, which scatters a part of the light guided in the thin-film lightguide, whereby a reference light field is produced. The invention further relates to an optical system having such a chip. The system is used for the marker-free analysis of particles, particularly biomolecules in their natural environment.

20 Claims, 6 Drawing Sheets

(51) Int. Cl.

| | |
|---|---|
| ***G02B 21/06*** | (2006.01) |
| ***G02B 21/16*** | (2006.01) |
| ***G02B 21/30*** | (2006.01) |

(52) U.S. Cl.

CPC ........... *G01N 33/557* (2013.01); *G02B 21/06* (2013.01); *G02B 21/16* (2013.01); *G02B 21/30* (2013.01); *G01N 21/6486* (2013.01); *G01N 2201/0231* (2013.01); *G01N 2201/08* (2013.01)

(56) References Cited

U.S. PATENT DOCUMENTS

| | | | | |
|---|---|---|---|---|
| 6,275,629 | B1 | 8/2001 | Eggleton et al. | |
| 6,483,096 | B1 | 11/2002 | Kunz et al. | |
| 7,289,224 | B2 * | 10/2007 | De Lega | G03F 7/70775 356/497 |
| 7,951,583 | B2 * | 5/2011 | Duer | G01N 21/553 385/12 |
| 8,288,157 | B2 * | 10/2012 | Duer | G01N 21/7703 436/805 |
| 2003/0016938 | A1 | 1/2003 | Hatayama et al. | |
| 2004/0091862 | A1 | 5/2004 | Brandenburg et al. | |
| 2004/0202420 | A1 | 10/2004 | Rogers et al. | |
| 2005/0057757 | A1 * | 3/2005 | Colonna De Lega | G01B 9/02022 356/497 |
| 2005/0153320 | A1 | 7/2005 | Herron et al. | |
| 2006/0044342 | A1 * | 3/2006 | Tajika | B41J 29/393 347/19 |
| 2006/0210232 | A1 | 9/2006 | Wu et al. | |
| 2007/0025658 | A1 | 2/2007 | Fukai et al. | |
| 2014/0178861 | A1 | 6/2014 | Duer | |
| 2018/0364174 | A1 | 12/2018 | Fattinger | |

FOREIGN PATENT DOCUMENTS

| | | | |
|---|---|---|---|
| CN | 104303089 | A | 1/2015 |
| CN | 107111169 | B | 6/2020 |
| CN | 112269225 | A | 1/2021 |
| CN | 112965166 | A | 6/2021 |
| DE | 69909480 | T2 | 4/2004 |
| DE | 10324973 | B4 | 4/2006 |
| EP | 0617273 | A2 | 9/1994 |
| EP | 0642052 | A1 | 3/1995 |
| EP | 2618130 | A1 | 7/2013 |
| JP | 2000-137197 | A | 5/2000 |
| JP | 2001-242430 | A | 9/2001 |
| JP | 2003-029219 | A | 1/2003 |
| JP | 2006-143529 | A | 6/2006 |
| JP | 2007-041142 | A | 2/2007 |
| JP | 4649788 | B2 | 3/2011 |
| KR | 10-0163738 | B1 | 4/1999 |
| KR | 10-2017-0055902 | A | 5/2017 |
| WO | WO-0153822 | A2 | 7/2001 |
| WO | WO-2006024314 | A1 | 3/2006 |
| WO | 2009/141390 | A1 | 11/2009 |
| WO | 2016/102693 | A1 | 6/2016 |

OTHER PUBLICATIONS

Boninsegna et al., Waveguide chip coupled with microfluidics enables super-resolution live-cell imaging, Spie Proceedings, vol. 11483, pp. 114830T-114830T (Aug. 2020).

* cited by examiner

OPTOELECTRONIC CHIP

Interferometric scattering microscopy (iSCAT) is a technique that uses the interference of light fields to detect particles with a size in the sub-wavelength range. To do this, the light that is elastically true to particles is superimposed with a reference light field and projected onto a detector such as a camera, where it interferes. Through spatially resolved detection of the interference contrast, information about the positions of the particles as well as their scattering cross-section can be extracted. This is related to the polarizability of the particles, which depends on both the particle mass and its chemical composition. The signal interference between the light scattered by the particle and the reference light enables optical detection of particles smaller than 5 nm with high temporal and spatial resolution, which is difficult or impossible with other non-interferometric optical imaging approaches.

iSCAT measurements can thus directly provide information about the relative distribution of different particle masses or their scattering cross-section in a sample solution without having to modify the particles to be examined, such as with a fluorescent marking. In addition, the absolute or relative concentration of particles, interactions between the same or different particles or individual components from its sample with unknown composition and their diffusion behavior can be determined, providing valuable information for biology or environmental science.

In practice, iSCAT microscopy uses high numerical aperture (NA) lenses in combination with immersion medium. In such an arrangement, the excitation light, the scattered light and the reference light follow the same optical path. The reference light is generated by a reflection of the excitation light at the boundary layer between the sample carrier and the sample. Since excitation and detection cannot be treated separately in this approach, the intensity of the reference light cannot be optimized to achieve the best interference contrast.

In addition, a great deal of effort must be expended to create a homogeneous illumination surface, which is essential for quantitative measurements with additional optoelectronic elements such as acousto-optical deflectors.

Another disadvantage of approaches based on high NA and high magnification lenses in combination with an immersion medium is that these measurement techniques are very temperature-sensitive, which means that temperature changes of only a few degrees Celsius greatly influence the imaging quality. Temperature-dynamic examinations thus become difficult to carry out. The integration of the illumination path on a chip in combination with a built-in heating element creates a monolithic device that is insensitive to temperature changes and that allows an extended temperature range to be examined, typically in the range of 0° to 100° C.

The scattering cross-section of particles in the sub-wavelength range scales with their radius to the power of 6 (Rayleigh scattering). The detection of small particles such as individual proteins on the basis of scattering microscopy is therefore an experimentally very demanding task. Interferometric scattering microscopy (iSCAT) helps to overcome these limitations, as the interference contrast produced by this approach is proportional to the volume of the particle. However, conventional iSCAT systems rely on high NA and high magnification lenses, which are expensive, not user-friendly and limit the effective field of view. Furthermore, the examination of dynamic temperature behavior is a difficult task, as a shift in focus is often observed. A monolithic waveguide chip that ensures local excitation near its surface (evanescent field) as well as the generation of a reference field without the need for the use of immersion oil opens up new avenues for robust, user-friendly and highly sensitive detection of single biomolecules over an extended temperature range.

Against this background, an object of the present invention is to mitigate or even completely eliminate the problems of the prior art.

In particular, the object of the present invention is to provide a device for performing interferometric scattered light microscopy that eliminates the need for a lens with a very high numerical aperture (>1) in combination with immersion medium and preferably also allows the sample to be set to a desired temperature reliably and quickly, as well as allowing larger observation fields of up to several $mm^2$ to be observed. A larger field of observation enables the parallel examination of different sample regions, which can also be physically separated from each other.

This object is achieved by an optoelectronic chip having the features of claim 1 and an optical system having the features of claim 11.

Advantageous further developments of the present invention are the subject matter of the sub-claims.

The present invention overcomes disadvantages of the prior art because the excitation and detection paths are fundamentally separate. The illumination profile here is defined by the mode profile of the guided mode and can be adjusted to create a very homogeneously illuminated active region. This approach allows the use of low magnification lenses (20×, 40×, 60×) to observe large region of up to several $mm^2$ with a resolution of less than 100 nm, well below half the wavelength of the excitation light, without the need for an immersion medium. However, the advantage of detecting the scattered light and the reference beam in the common path remains. Since the evanescent field of the waveguide mode only penetrates a highly selective region of about 100 nm of the sample volume, background signals present in conventional iSCAT experiments are suppressed and the total optical power required for illumination is reduced to a minimum. Unwanted effects such as sample heating, light-induced protein degradation or cellular phototoxicity are thus reduced.

An optoelectronic chip according to the invention for receiving a sample for optical examination, has a carrier layer, a thin-film lightguide having an active region, in which the sample interacts with a guided mode of the thin-film lightguide, wherein at least one scattering structure is arranged in the active region, which scatters the light guided in the thin-film lightguide, whereby a reference light field (also referred to as a reference beam) is produced. In the following, the terms "lightguide" and "waveguide" are used, which are preferably to be understood as synonyms in the context of this application.

Preferably, the scattering structure is regular and/or irregular and extends partially or completely over the active region. The scattering structure can be regular in sections and irregular in sections. Examples of the scattering structure comprise:

a) a spatially periodic modulation of the effective refractive index of the lightguide by a 1D grating structure. This grating structure can be made by layer thickness modulation of the lightguide layer or other layers close to the lightguide.

b) a spatially periodic modulation of the effective refractive index of the lightguide mode by a 2D periodic structure.

c) a spatially random modulation of the effective refractive index of the lightguide mode due to surface roughness of the waveguide layer caused by the coating process or surface roughness of the carrier structure (typ. <10 nm rms) a.

b. distributed, for example dispersed, scattering centers, such as nanoparticles, in the lightguide layer or one of the layers near the lightguide, which lead to a random or periodic modulation of the effective mode index.

In other words, the scattering structure is preferably formed by varying the effective mode index of the waveguide regularly and/or irregularly in a predetermined range. For example, the mode index of the waveguide can be varied locally in a regular periodic pattern.

According to one embodiment of the invention, the scattering structure is designed as a surface roughness.

A periodic modulation of the effective refractive index of the optical fiber mode leads to a selective diffraction or scattering of the light guided in the waveguide in the direction of a detector, e.g. a detector of an optical system or microscope.

Randomly distributed scattering centers, such as surface roughness, lead to a non-directional generation of the reference field.

An optoelectronic chip according to the invention can have several lightguides, which can be arranged next to each other and/or one above the other.

For example, a first lightguide can be provided, which is also referred to as a measuring lightguide, and interacts with a sample. In addition, a second lightguide, also referred to as a reference lightguide, can be provided, which extracts a certain amount of the light of the guided mode of the measuring waveguide and leads it to an outcoupling region.

The scattering structure is preferably provided or arranged on or in the measuring lightguide. By means of the reference lightguide, the intensity of the light guided in the measuring lightguide can be detected or monitored and, for example, controlled or regulated by an optical system or microscope on the basis of the detection results.

Furthermore, it has proven advantageous in practice if an optoelectronic chip according to the invention is equipped with a coupling region for coupling out a guided mode from the thin-film lightguide. This is used to monitor the intensity of the guided mode. The light coupled out by means of this coupling region is fed to a sensor for intensity measurement via a reference lightguide, for example. Thereupon, a control device can be used to control or regulate the intensity of the light of the guided mode of the thin-film lightguide.

For example, the reference waveguide extracts a portion of the guided light of the measurement waveguide via evanescent coupling to the measurement waveguide. Any other type of coupling, for example via a splitter, is also conceivable.

Preferably, the extraction of the light for the reference waveguide occurs when viewed along the propagation direction of the light in the sensing waveguide before the active sample region of the sensing waveguide. This ensures that the amount of light emitted into the sample volume remains constant regardless of the sample volume. It may be advantageous to perform the light extraction in a region of the measuring waveguide where only a single mode is supported by the waveguide.

The detection of the light scattered from the reference arm or reference lightguide can be carried out with a photodetector. By electronically amplifying the signal, the power of a light source, for example a laser diode, which feeds light into the measuring waveguide, can be controlled. In this way it is possible to compensate for variations in intensity caused by environmental fluids, mechanical vibrations and movements that the light may experience, for example in an optical fiber, between the light source and the measuring waveguide.

An optoelectronic chip according to the invention can be used for receiving a sample for optical examination, wherein a sample, preferably an at least partially liquid, solid or gel-like sample is applied to the optoelectronic chip in such a way that the sample partially or completely surrounds the active region of the thin-film lightguide.

For this purpose, the sample contains at least one or a plurality of particle(s) that is/are capable of and/or designed to interact with a guided mode of the thin-film lightguide.

Another aspect of the present invention relates to an optical system adapted to be used with an optoelectronic chip according to the invention and adapted to generate interference between the scattered light of at least one particle located in the sample space and the reference light generated by the scattering structure, i.e. the light deflected by the scattering structure.

Furthermore, an optical system according to the invention, which is adapted to be used with an optoelectronic chip according to the invention, is adapted to image the generated interference on a detector.

An optical system according to the invention comprises at least one light source for feeding light into the at least one thin-film lightguide, preferably the measuring waveguide. If an optoelectronic chip according to the invention with a plurality of measuring waveguides is used, the optical system preferably has a plurality of light sources, each of which is assigned to a measuring waveguide. The light sources can emit light of the same or different wavelengths.

In other words, light from one or a plurality of light sources of the same or different wavelengths is sent to the coupling regions of the waveguides either via free-beam optics or by means of optical fibers and micro-optics. In this way, different or the same wavelengths can be coupled into different measuring waveguides either simultaneously or with a time delay. Each measuring waveguide preferably has at least one reference waveguide, which makes it possible to measure and individually control the intensity of the guided light in the respective measuring waveguides via separate photodetectors.

The reference light and the scattered light, which is scattered in the active region orthogonally to the propagation direction in the waveguide, are preferably imaged via an optical system onto a 20 array detector and the optical system is preferably a microscope.

An optoelectronic chip and/or optical system according to the invention are used, for example, to determine antigen-antibody binding affinity, to examine antibody-antibody cross-linking and/or multi-site binding processes, to analyze protein-protein interactions, to estimate protein sizes, in the context of examinations on protein degradation and denaturation properties, and to optimize and characterize formulations.

In other words, the present application describes the technical details of an optical chip designed for use within an optical microscope to detect individual particles (e.g. antibodies, viruses, etc.) with a diameter smaller than the excitation wavelength in solution or thin films with respect to a reference signal and to detect their individual scattering cross-section and/or particle mass in a parallelized imaging modality in a spatially and temporally resolved manner.

An optical chip or optoelectronic chip that has a thin-film lightguide (also known as a waveguide) can be considered a key component. Within an active region of the waveguide, the supported waveguide mode can interact with nanoparticles near the surface of the waveguide (evanescent field). The light scattered by the nanoparticles is collected with a lens system and thus directed onto a detector (e.g. a camera).

The scattering signal of the particles is amplified by exploiting an optical reference field generated on the chip near the position of the nanoparticle by means of a scattering structure.

Both the reference light generated by the scattering structure (also referred to as the reference field or reference beam) and the scattered light from the particles (also referred to as the scattered field) are collected with the same optics and detected on the same detector where they interfere.

The excitation light, which is necessary to generate the reference field and to interact with the nanoparticles, preferably passes through the same optical path to the detector (e.g. a camera). In this way, the phase relationship between the scattered field and the reference field is maintained regardless of external influences, which makes the system robust. With a spatially and temporally resolved detection of the interference pattern, time-dependent particle positions as well as their scattering cross-section can be determined.

The reference light field for interference is generated on the chip by defined (e.g. periodic or regular) or undefined (random structures, surface roughness) structures within and/or along the active region of the waveguide structure.

The strength of the reference light field is selected to optimize the interference contrast on the detector, the signal-to-noise ratio and/or the maintenance of a propagation mode within the waveguide chip.

The light intensity of the reference light field can be adjusted in connection with the intensity of the mode guided in the waveguide by the type of scattering structure in such a way that the resulting interference signal enables optimal localization of the particle to be analyzed in all three spatial directions at any given time. Parameters that determine the ideal strength of the reference field are, for example, the wavelength of the light, the scattering cross-section of the particle, the integration time of the detector, the signal strength on the detector, visual noise and diffusion speed or residence time of the particle.

The average signal detected by the detector is several orders of magnitude higher than the scattered signal of the nanoparticle alone due to the joint detection of the scattered light of the particles and the reference light of the scattering structures, which increases the contrast, shortens the detection time and therefore also enables the detection of fast-moving, small particles (<5 nm).

The measurement can be performed with multiple wavelengths to increase precision and to avoid absorption in the medium/particle and/or can be combined with a fluorescence detection channel.

The scattering cross-section is a function of the wavelength. Shorter wavelengths have the advantage that the scattering cross-section is increased while the particle size remains the same and thus leads to a stronger signal. At the same time, different wavelengths have different penetration depths into the sample volume, so that the axial position of the particle can also be determined by a wavelength-dependent measurement.

An optoelectronic chip according to the invention is used, for example, for receiving a sample in the visualization of temperature-dependent processes and can generally be regarded as an object carrier.

An optoelectronic chip according to the invention, according to an embodiment optimized for the visualization of temperature-sensitive processes preferably has a carrier layer, a lightguide (hereinafter also referred to as waveguide), preferably a thin-film lightguide, and a heating element, preferably a thin-film heating element, wherein the lightguide and the heating element are preferably arranged on opposite sides of the carrier layer.

Where the term thin-film lightguide is used, it is to be understood that this reflects only a preferred embodiment and that other lightguides are also encompassed by the invention. Where the term thin-film heating element is used, it is to be understood that this reflects only a preferred embodiment and that other heating elements are also encompassed by the invention.

The heating element and/or the lightguide is/are preferably optically transparent. In a chip according to the present invention, such a heating element is optional.

Optically transparent material is here preferably rather permeable to light in the range visible to humans, wherein the transmission of light through the optically transparent material is preferably at least 0.5, in particular at least 0.8. Optically opaque material is here preferably rather impermeable to light in the range visible to humans, wherein the transmission of light through the optically opaque material is preferably at most 0.49, in particular at most 0.3.

The lightguide and/or the heating element can be arranged directly on a surface of the carrier layer or be spaced apart from it via one or more intermediate layers.

In addition, the lightguide and/or the heating element and/or the carrier layer can each be designed as a single layer or as a composite of two or more sub-layers.

Preferably, the carrier layer consists completely or at least partially of an opaque or transparent material, preferably of Si or another $SiO_2$-based glass or crystal.

The carrier layer thus consists, for example, of glass, in particular borosilicate glass, and is preferably designed to give the optoelectronic chip mechanical stability.

Furthermore, between the carrier layer and the thin-film waveguide there can be a further transparent layer that has a lower refractive index than the carrier layer, preferably a refractive index between 1.0 and 1.5.

According to one embodiment of the invention, the carrier layer is made entirely or at least partially of a semiconductor material, preferably $SiO_2$, and preferably a transparent layer, in particular a separating layer, is further present between the carrier layer and the lightguide, preferably the thin-film lightguide.

Furthermore, the thin-film heating element is preferably connected to and/or equipped with a temperature sensor, preferably in the form of a thin-film temperature sensor, which is designed to come into direct or indirect contact with a sample.

For example, within the temperature sensor, a sensor layer for detecting the temperature of the sample may be provided, which preferably has metal and/or is made of metal and which preferably at least partially covers an outer surface of the optoelectronic chip and is further preferably designed to come into contact with a sample. The temperature sensor can be in direct or indirect contact with the sample.

Preferably, the temperature is measured by the temperature sensor at at least one location in the sample, preferably at a plurality of locations to provide a more reliable reading.

Preferably, a four-wire measurement is used within the framework of the temperature sensor.

Another option is to determine the temperature via an infrared sensor from a distance.

Furthermore, the optoelectronic chip preferably has a control unit to control and/or regulate the thin-film heating element on the basis of the measurement data regarding the sample temperature acquired by means of the temperature sensor.

Preferably, a thin-film heating element used in the invention is or comprises a resistance heating element. For example, carbon nanotubes can also be used in the frame of the heating element.

In order to ensure that particles and/or objects and/or molecules to be examined can be localized close to a surface of the optoelectronic chip and thus in the range of the evanescent waves, it has proven advantageous in practice if an outer surface of the optoelectronic chip, which is designed to come into contact with a sample, at least partially or completely has a surface modification, surface functionalization or the possibility of surface functionalization, in order to bind molecules (or other particles and/or objects) contained in the sample, in particular biological molecules.

For example, surface functionalization may involve providing the surface with certain functional chemical groups, such as hydroxy groups, to specifically bind a desired class of molecule to the surface.

The present invention further relates to a use of an optoelectronic chip according to the invention for receiving a sample in the visualization of temperature-dependent processes, wherein a sample, preferably an at least partially liquid, solid or gel-like sample is applied to the optoelectronic chip in such a way that the sample partially or completely covers the thin-film lightguide and preferably also the sensor layer of the temperature sensor. Furthermore, a chip according to the invention can be used with a microfluidic system.

For example, an optoelectronic chip according to the invention can be used to observe a temperature-sensitive process at a precisely controlled temperature of the sample. An optoelectronic chip according to the invention can further be used to examine the temperature dependence of a process by observing the process at different precisely controlled temperatures of the sample.

The sample used in the present invention preferably contains at least one or a plurality of particles and/or objects and/or molecules that are capable of and/or designed to interact with a guided mode (also referred to as mode) of the thin-film lightguide. For example, the molecules are excited to fluoresce by the light guided or conducted by the lightguide, deflect this light and/or absorb the light.

A further aspect of the invention relates to an optical system, preferably a microscope, particularly preferably a TIR microscope, which is adapted to be used with an optoelectronic chip according to the invention.

An optical system according to the invention preferably has at least one emitter that emits light for optical excitation into the thin-film waveguide and at least one detector that detects light deflected and/or emitted by the sample normal to the plane of the thin-film waveguide.

This design physically separates the light paths for excitation of the sample and detection of the light, reducing general scattered light that occurs when light is coupled into the waveguide or guided in the waveguide, and scattered light due to local scattering of light by the sample and background light. This leads to an improved ratio between the desired detected signals from the sample and unwanted signals caused by the measurement setup.

In order to guide light in a mode typical for the optical waveguide, coupling modules such as grating couplers, prism couplers and/or direct coupling mechanisms between two optical waveguides are preferably used. These coupling modules are used to introduce external light into the waveguide. More efficient coupling modules can reduce the general scattering background here.

One or more lightguides (measuring waveguides) guide the light onto or through an optoelectronic chip according to a preferred embodiment and thus also through the volume of the sample.

The light guided by the measuring waveguide can be reflected back and/or coupled out. For this purpose, coupling modules such as grating couplers, prism couplers and/or direct coupling mechanisms between two optical waveguides are preferably also used.

It is also conceivable that an optical mode of a different wavelength propagating simultaneously through the lightguide, different optical modes of the same wavelength or their combination are guided by means of additional coupling modules. An interaction of these within the waveguide and their detection can be used for highly sensitive measurements of the refractive index on the chip surface.

The temporal analysis of the transmission or reflection signal of one or the measurement waveguides can be used in addition to correlation measurements and fluctuation measurements (similar to dynamic light scattering—DLS).

Preferably, in an optical system according to the invention, the detector is an array detector and/or the optical system is a microscope.

The invention further relates to a use of an optoelectronic chip according to the invention and/or of an optical system according to the invention for determining a phase transition of a particle (organic or inorganic) contained in the sample or of a spatially extended material. This phase transition may involve, for example, the modification of a biological molecule, such as an enzyme, a protein or a deoxyribonucleic acid (DNA) or ribonucleic acid (RNA).

Another aspect of the invention relates to a use of an optoelectronic chip according to the invention and/or an optical system according to the invention in the context of high-throughput sequencing, preferably based on single molecule analysis.

Yet another aspect of the invention relates to a use of an optoelectronic chip and/or optical system according to the invention for examining the binding affinities between at least one protein and at least one antibody as a function of temperature and/or other external stimulants such as salt or buffer concentrations. The invention further relates to a use of an optoelectronic chip according to the invention and/or an optical system according to the invention for the examination of living cells under temperature-controlled conditions and their interactions with individual particles. Interactions between proteins and/or interactions between proteins and small molecules can also be examined with an optoelectronic chip and/or an optical system according to the invention.

In summary, the present invention can achieve at least the following advantages:

An optical microscope can be created that contains an optical chip according to the invention that amplifies the scattering signal from small particles such as viruses, proteins and other nanoparticles that are in the evanescent field of the waveguide. This is achieved by creating a reference light path that interferes with the scattered light originating from the analytes in the sample on the detector. When the interference signal is detected on a camera, for example, small biomolecules with a low mass (<500 kDa) or a small radius of less than 5 nm can be detected.

A chip according to the invention is particularly user-friendly and compact due to the monolithic chip design, in particular the compact and robust design of the chip, for the evanescent excitation of scattering particles (nanoparticles) and for the generation of reference light.

In addition, a chip according to the invention is suitable for generating a homogeneous sample illumination area (active area) and a reference beam.

In addition, a chip according to the invention can be used in combination with an optical system that projects the scattered and the reference beam onto a detector where the interference signal is analyzed with temporal and spatial resolution.

In addition, a chip according to the invention enables highly selective excitation of a small sample volume above the waveguide in the axial direction (evanescent field, typically 100 nm above the waveguide) and over up to several $mm^2$ in the sample plane. The optical chip can contain a plurality of or one measuring waveguide with different active regions and can be used in combination with fluorescence measurements.

The decoupling of the excitation beam path from the detection beam path enables particularly clean optical detection by means of a chip according to the invention.

The use of a chip according to the invention also allows the use of low magnification lenses (e.g. 20×, 40×, 60×) to image large areas up to several $mm^2$ without the need for immersion oil, although it is still possible to use this.

In addition, in the context of a chip according to the invention, the reference beam was optimized for optimum interference contrast generation. Furthermore, a chip according to the invention enables dynamic temperature studies over an extended temperature range (preferably from 0° C.-100° C.).

In addition, in the context of the present invention, spatial resolution is maintained up to the diffraction limit and/or even below (super-resolution).

Furthermore, the present invention is preferably characterized by at least one or also several of the technical features listed below:

Preferably, a chip according to the invention comprises a thin-film waveguide with a thickness of preferably less than 5 μm (typ. <300 nm, in particular between 30-300 nm) on a transparent (e.g. $SiO_2$) or non-transparent material (e.g. Si); the latter must be combined with a transparent separating layer (e.g. as an SOi system).

Preferably, a chip according to the invention further comprises at least one scattering structure within the active region of the waveguide that generates a reference light field that allows interference with the light scattered by the particle on a detector. In addition, a chip according to the invention comprises an active region of the optical waveguide in which the sample volume can interact with the evanescent field of the guided mode.

It is also possible to integrate several measuring waveguides with separate active regions on one chip.

Furthermore, a collection lens or detection lens is preferably provided for directing the scattered and the reference light field to a detector (e.g. camera).

Preferably, the emitted and scattered light from the active area is detected with a 2D array detector (e.g. camera) that detects the light perpendicular to the waveguide plane via the collection lens.

In a chip according to the invention, coupling modules for coupling free-space light modes into the supported waveguide mode and/or decoupling modules are also preferably provided, which enable active intensity feedback of the light guided in the waveguide.

A chip according to the invention can be designed for receiving a sample volume in the range of 0.1 μl to several hundred μl (e.g. microfluidic channels).

Optionally, simultaneous detection of fluorescence takes place via a separate detection path or at different wavelengths in the same detection path alongside interference microscopy, in particular interferometric scattering microscopy (iSCAT).

If a chip according to the invention is equipped with a heating element, this enables local and direct heating and thus exploitation of fast temperature dynamics. This results in high temperature stability and large heating and cooling rates of up to 100 K/s.

Furthermore, within the scope of the present invention, optical excitation of parts of the sample volume via free-beam optics may be provided.

Optionally, optical or electrical manipulation of the sample (e.g. by a laser trap, electrostatic trap, etc.) may also be provided within the scope of the present invention.

Preferably, the present invention utilizes at least one or more of the physical effects listed below:

Interference: A small scattering signal from nanoparticles is amplified by interference between scattered light from the particle and reference light generated on the chip. The interference signal is detected by a photodetector (e.g. camera). Spatial and temporal information about the positions of the particles and their scattering cross-section is extracted from this.

Fixed phase relationship: On-chip generation of reference fields and their imaging via a common collection optics ensures a fixed phase relationship between the light scattered by the particles and the reference field.

Evanescent excitation field: Preferably, an excitation of scatterers/absorbers/emitters takes place in the optical near field of a thin-film waveguide. Preferably, a strongly limited and well-defined excitation volume is created by the evanescent wave generated at the surface of the waveguide (penetration depth into the sample volume approx. 100 nm). The decay of the evanescent wave in the normal direction to the propagation of the waveguide mode can be smaller than the free space wavelength of the excitation light.

Further advantages, features and effects of the present invention are shown in the following description of preferred exemplary embodiments with reference to the figures, in which the same or similar components are designated by the same reference numerals. In the figures.

Figure 2:
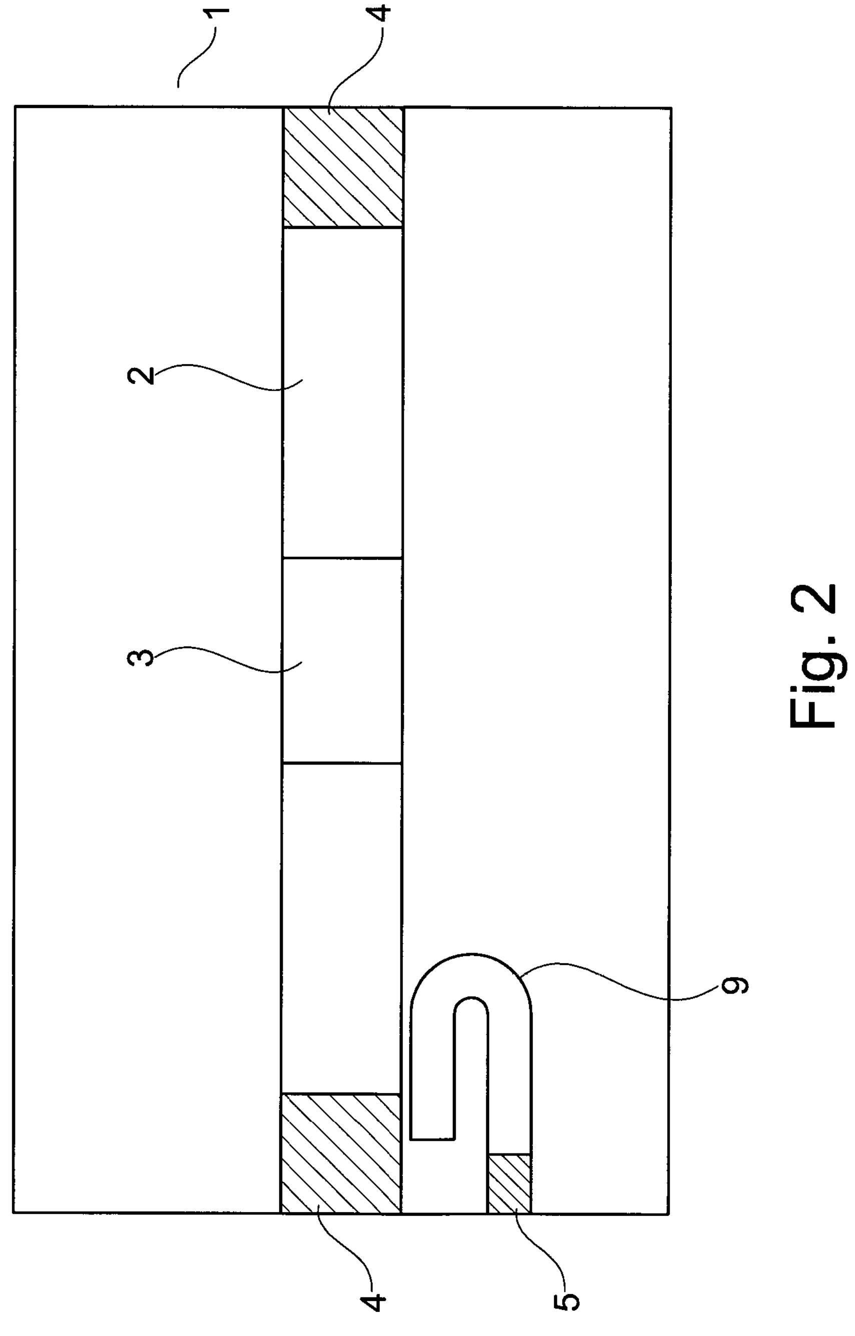
FIG. 2 shows an optoelectronic chip according to the invention with a representation of the light coupling interfaces as well as the interfaces in the waveguide required for light intensity measurement.
Figure 2A:
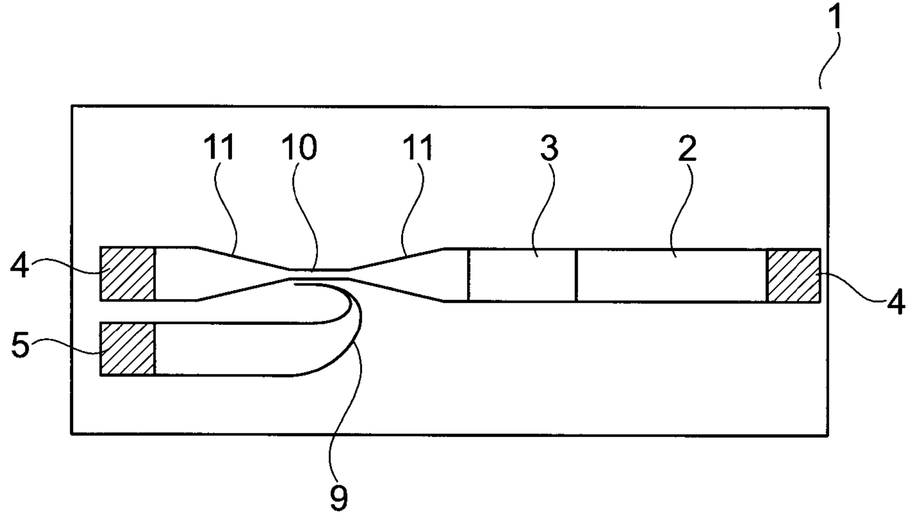
Figure 3:
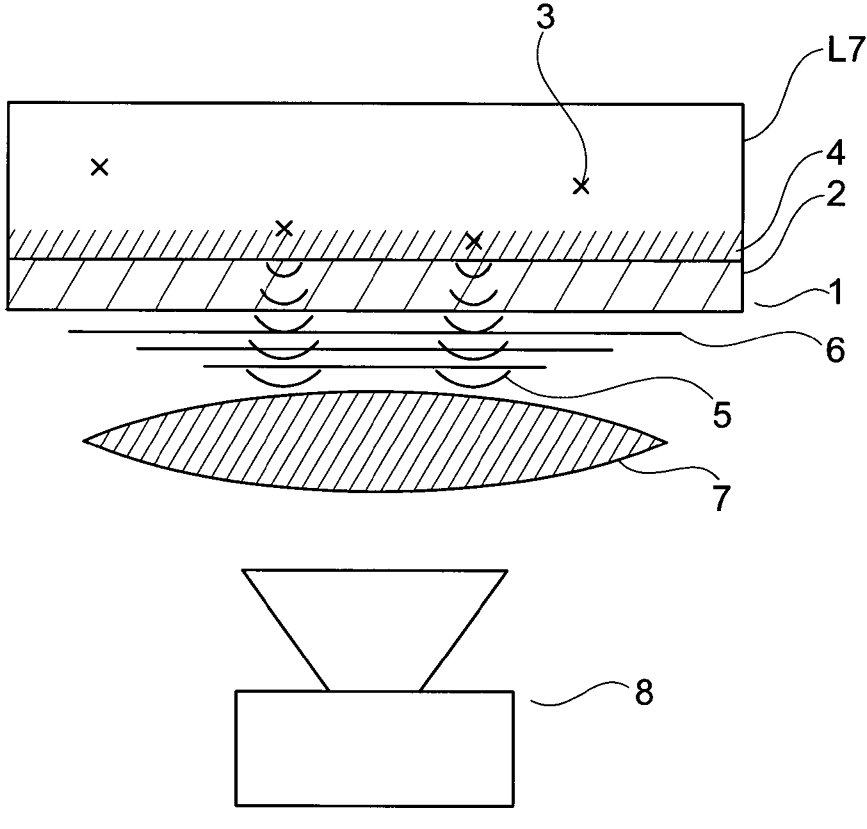
Figure 3A:
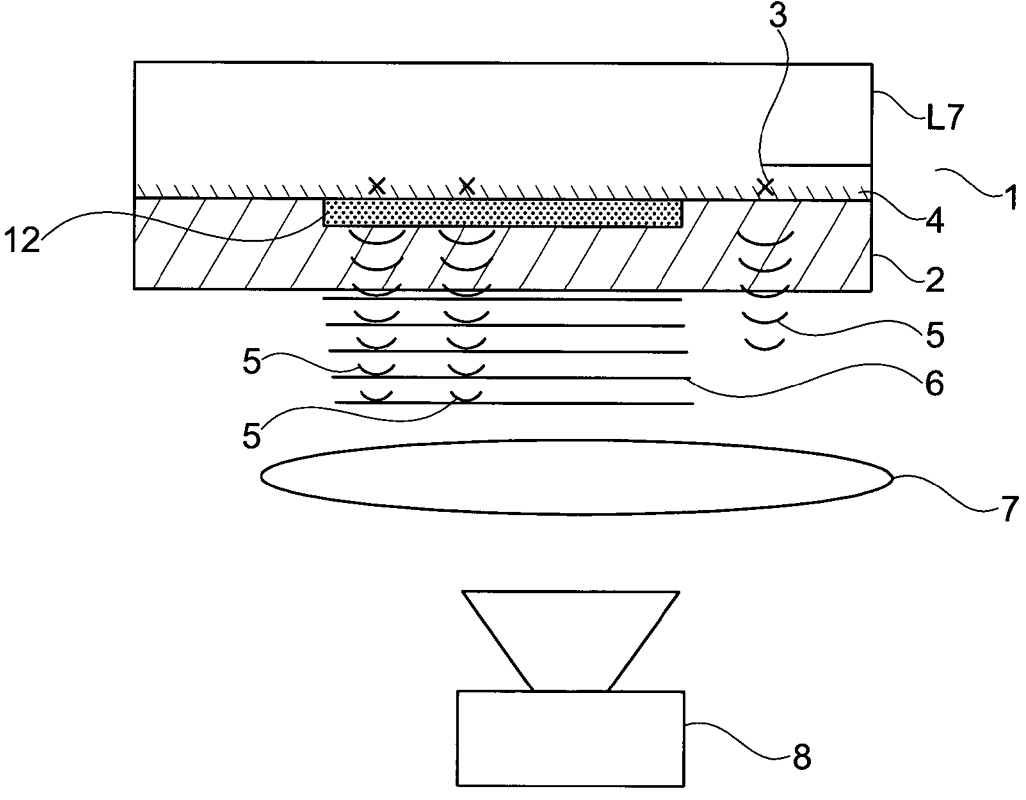

FIG. 2*a* shows an optoelectronic chip according to the invention with a structure for mode purification;

FIG. 3 shows the principle of on-chip interferometric detection as performed in the context of the present invention, FIG. 3*a* additionally shows a scattering structure for producing a reference light field; and FIG. 3 shows the construction of an optical system according to the invention, in particular a microscope.

Figure 1:
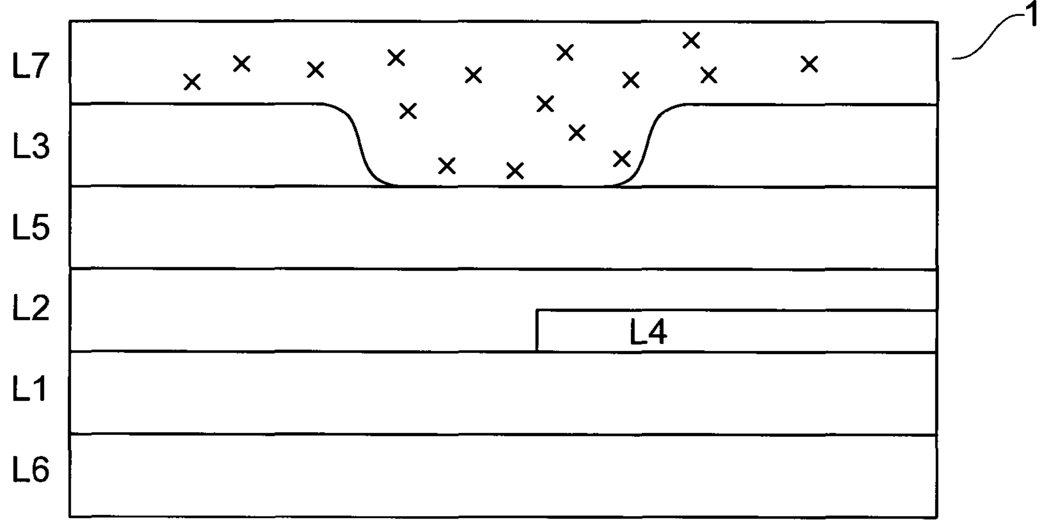
FIG. 1 shows a schematic representation of the layer construction of a chip according to the invention.

FIG. 1 shows an optoelectronic chip 1, which has up to seven layers (L1-L7). In this embodiment, all layers preferably have a surface roughness of less than 5 nm rms. All layers can be structured independently in the substrate plane, e.g. with grating couplers for diffraction of the incident free beam into one of the guided modes. The waveguide layer L5 can be chemically functionalized, e.g. for the specific binding of biomolecules.

The layer L1 has or consists of a carrier material, in particular a transparent glass substrate (e.g. borosilicate, quartz glass, etc.) with a thickness between 50 and 1000 μm and a refractive index of $n_{sup}$ or a semiconductor material (e.g. Si) in combination with a transparent separating layer.

Optionally, a transparent layer L2 can be provided as a separating layer, wherein the layer L2 has a refractive index of $n_{sp1}$, where preferably $n_{sp1}<n_{wg}$. The layer L2 can be made up of several sub-layers.

Alternatively or additionally, an optionally transparent layer L3 can be provided as a separating layer, wherein the layer L3 has a refractive index of $n_{sp2}$, where $n_{sp2}<n_{wg}$. The layer L3 can be made up of several sub-layers.

For the integration of a thin-film resistance temperature sensor, an additional layer L4, preferably a metal layer, can be applied either on the separating layer L2, the separating layer L3 or on the carrier material of the carrier layer L1. The layer L4 can consist of metal lower layers. The layer L4 preferably only extends over a partial region of the adjacent layers; in this example the layers L1 and L4.

The layer L5 has or consists of a waveguide. The layer L5 is used as a highly refractive, non-absorbing layer with a refractive index of preferably $n_{wg}>n_{sup}$. The layer thickness is preferably between 30 and 600 nm. The layer L5 preferably comprises or consists of materials such as $TiO_2$, $Ta_2O_5$, $Al_2O_3$, $Nb_2O_5$, $Si_3N_4$, GaP, $ZrO_2$, $SiO_2$, etc. The layer L5 can consists of several sub-layers of different materials.

Optionally, a layer L6 can be provided as a heating element. The layer L6 is preferably a transparent conductive layer with a thickness of 1 nm-100 nm and is designed as a resistance heater, i.e. it preferably has materials such as ITO, carbon nanotubes, etc. for resistance heating.

The layer L7 reflects the sample volume. This volume contains particles that interact with the guided mode of the waveguide layer. The sample can be liquid, solid or gel-like and preferably partially or completely surrounds the waveguide.

The functionality of an optoelectronic chip according to the invention is explained below with reference to the representation in FIG. 2.

FIG. 2 shows a top view of an optoelectronic chip 1 according to the invention, in which a waveguide structure 2 and an active region 3 of the chip 1 are visible.

In the chip shown in FIG. 2, a substrate is coated on one side with a patterned waveguide layer that supports single or multiple waveguide modes with significant power ratio outside the waveguide layer itself (>1%). Within the active region 3 of the waveguide 2, the guided light can be scattered, absorbed or/and re-emitted by particles within the sample volume. A reference light field is generated within the active region 3 of the waveguide 2 by selectively or non-selectively coupling out parts of the guided mode in the direction of the collection lens (also referred to as detection lens). The waveguide (lightguide) 2 corresponds to a measuring waveguide (measuring lightguide).

This can be achieved, for example, by introducing a certain surface roughness or a periodic structure (e.g. a grid) within the active region 3, preferably within the layers L1, L2 and/or L5, which are used as a scattering structure and create a reference light field.

The scattering structure preferably overlaps spatially with the active region, in particular when viewed along the light used as a reference beam.

The amount of light injected into the reference beam path is preferably selected in such a way that the interference signal of the nanoparticles on the detector is optimized in terms of contrast, signal-to-noise ratio and visual noise for a given integration time of the detector.

The width of a waveguide of an optoelectronic chip according to the invention (for example, the dimension from the upper edge of the waveguide 2 or 9 to the lower edge of the waveguide 2 or 9 in FIG. 2) 2 is preferably between 100 nm and 1000 μm.

The dimension of a chip 1 according to the invention is preferably 30×20 mm. It has been found advantageous if a chip 1 according to the invention is smaller than 50 mm×50 mm and larger than 5 mm×5 mm.

The on/off coupling of waveguide modes in the chip 1 of FIG. 2 according to the invention is preferably performed as follows: Coupling regions 4 enable the coupling in and out of free space modes into or out of the waveguide mode. The chip 1 may contain one or more coupling regions 4 and one or more waveguides 2. A coupling region 4 is preferably provided to couple into a waveguide mode.

An additional coupling region can be used as a reference coupling region 5 to couple a certain portion of the guided light back into free space modes in order to monitor the light intensity propagating within the guided mode. In other words, the reference coupling region 5 selectively couples light out of the waveguide 2 so as to monitor the light intensity. A reference waveguide (reference lightguide) 9 is provided for this purpose. The outcoupled light can be used to stabilize the intensity within the guided mode either before or after the active region.

FIG. 2*a* shows an optoelectronic chip according to the invention with a structure for mode purification. The mode purification can take place via a single mode taper. In this case, the guided mode in the measurement waveguide can be purified by an adiabatic transfer 11 into the single-mode regime, so that multi-mode interference can be avoided and homogeneous sample illumination can be ensured. In FIG. 2*a*, the reference numeral 10 indicates a single-mode region in which a single mode is present. After the transition to the single-mode regime, the measuring waveguide 2 can again be adiabatically expanded by an adiabatic transition 11, such that a sample range of several 100 $\mu m^2$ up to several $mm^2$ can be excited. The single-mode region 10 can be used simultaneously to extract a certain amount of light from the waveguide for intensity monitoring by means of a reference waveguide 9, for example via evanescent coupling.

The detection of particles in the sample volume is shown schematically in FIG. 3 and is preferably carried out as follows: Particles 3 in the sample volume L7 and in the immediate vicinity of the waveguide 2 (layer L5) of the chip 1, i.e. within the evanescent field 4 of the waveguide 2, can interact with the propagation mode.

The light 5 scattered by the particles 3 as well as, if applicable, fluorescence signals of the particles in combination with the reference beam or the reference light 6 generated by means of the scattering structure is collected with optical elements (e.g. a lens 7) orthogonally to the propagation direction of the waveguide 2 on one or both sides of the waveguide (for example above and below the chip).

The signals are then projected onto a detector, e.g. the camera 8, where the coherent signals, in particular the light 5 scattered by the particles and the reference light 6, interfere. The optional fluorescence signal that is still present can be separated with optical filters and simultaneously projected onto another detector (not shown here).

FIG. 3*a* also shows a scattering structure 12 which is arranged on the surface of the waveguide 2 (measuring waveguide) and generates the reference light field 6. The scattering structure is embedded in the waveguide 2, for example, and may be produced by a surface etching of the waveguide 2. In principle, the scattering structure can be formed by applying and/or introducing surface modification to or into a surface of the waveguide 2, e.g. in the form of tiny protrusions or recesses.

Optionally, an optically transparent heating element can be used to control the temperature of the chip via resistance heating. Furthermore, an additional temperature sensor could be built into the waveguide structure to provide direct temperature feedback. This embodiment is particularly advantageous when temperature-sensitive processes are to be observed.

The probability of finding particles within the excitation volume can be based on Brownian motion, convection, gravity or determined via a specific or non-specific interaction potential caused by special surface properties (e.g. coatings, functionalizations, etc.) or external optical or electrical forces.

Preferably, one or more of the following functional elements are arranged on a chip according to the invention:

Coupling and decoupling structures of the waveguide: The waveguide mode is excited via coupling structures or coupling modules such as grating couplers, prism couplers or direct fiber coupling mechanisms. The waveguide mode is preferably transmitted via the chip including the sample volume. The transmitted mode can be reflected back or coupled out with similar arrangements as the coupling module. A waveguide mode propagating simultaneously or separated in time in another direction can be coupled in with additional coupling modules.

In the waveguide, a special decoupling structure is preferably implemented for the intensity measurement of the guided light, which allows the light intensity guided in the waveguide to be monitored in interaction with the sample volume. This intensity reference can be detected via a light-sensitive element and used to actively stabilize the intensity.

The intensity of the measuring waveguide can also be detected in transmission and used for auto-correlation measurements similar to dynamic light scattering (DLS).

In the active region of the chip, the sample volume comes close to the waveguide. Particles within the sample volume that interact with the guided light (evanescent field) produce fluorescent and/or scattered light. A certain structure within this area generates a reference light field that can also be detected by the detection system and that allows interference with the light scattered by the nanoparticles in the sample volume.

Furthermore, a heating element may be provided in a chip according to the invention. The heating element preferably consists of or comprises an optically transparent, conductive thin film (e.g. ITO). For example, by applying a direct current, heat is generated which is transported through the carrier material into the sample volume. The heating element is preferably locally limited to the sample volume. Metallic electrodes, for example, allow connection to an external electronic heating circuit.

A temperature sensor can also be provided. Temperature detection for the heating circuit can be realized in particular with a thin-film resistance temperature sensor (e.g. Pt sensor) integrated on the chip. The temperature sensor is preferably read out via a four-point measurement. The sensor is preferably positioned between the heating element and the sample volume or on the top side or a side of the waveguide layer facing away from the carrier layer (separating layers are required).

Figure 4:
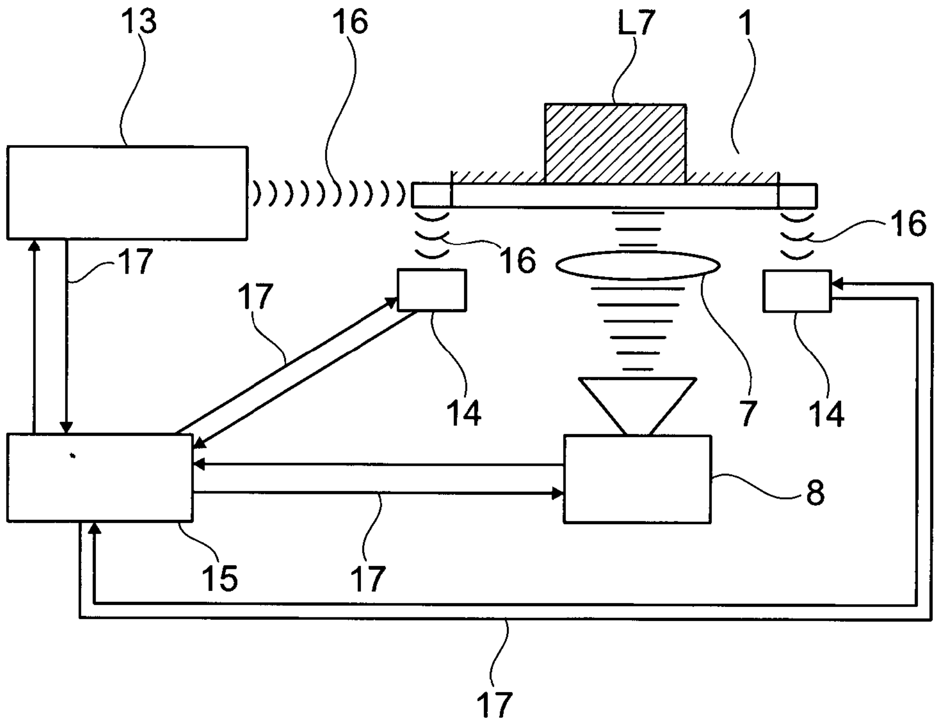

FIG. 4 schematically shows the construction of an optical system according to the invention, in particular a microscope. The microscope has at least one light source 13 which feeds light into a measuring waveguide 2 of the optoelectronic chip 1. The intensity of the light guided into the measuring waveguide 2 is detected by means of two photodetectors 14, for example by coupling the light out of the measuring waveguide 2 via a reference waveguide 9 and feeding it to a photodetector. The optical signals designated with reference 16 in FIG. 4 can be transmitted as free beams and/or e.g. in fibers.

Both the light source 13 and the photodetectors 14 are connected to a control unit 15 that can control or regulate the light source 13, for example, on the basis of the light intensities detected by means of the photodetectors 14. For this purpose, the control unit 15 is connected to the light source 13 and the photodetectors 14 via bidirectional data lines 17. The camera 8 or imaging lens is also connected to the control unit via bidirectional data lines 17.

The present invention is particularly useful in the detection of individual particles and the analysis of particle dynamics. Exemplary applications are: the determination of antigen-antibody binding affinity, antibody-antibody cross-linking and multi-site binding processes, the analysis of protein-protein interactions, the estimation of protein sizes (hydrodynamic radius), investigations on protein degradation and denaturation properties, as well as the optimization and characterization of formulations (e.g. vectors of the adeno-associated virus (AAVs), nanoparticles, etc.).

The invention claimed is:

1. An optoelectronic chip for receiving a sample for optical examination, having a carrier layer, a thin-film lightguide having an active region, in which the sample interacts with a guided mode of the thin-film lightguide, wherein at least one scattering structure is arranged in the active region, which scatters light guided in the thin-film lightguide, whereby a reference light field is produced, wherein the chip further comprises a periodic structure within the active region.

2. The optoelectronic chip according to claim 1, wherein the scattering structure is formed regularly or irregularly and extends partially or completely over the active region.

3. The optoelectronic chip according to claim 1, wherein the scattering structure comprises local variations in an effective refractive index of the thin-film lightguide or a layer interacting with the guided mode.

4. The optoelectronic chip according to claim 1, wherein the reference light field is produced by light-scattering particles interacting with the mode guided in the lightguide layer.

5. The optoelectronic chip according to claim 1, wherein the thin-film lightguide further has a structure for mode purification.

6. The optoelectronic chip according to claim 5, wherein the structure for mode purification comprises means of at least one adiabatic transition, limits the light guided in the thin-film lightguide to a single mode, at least in sections.

7. The optoelectronic chip according to claim 1, which contains an optically transparent thin-film heating element in addition to the thin-film lightguide.

8. A method of receiving a sample for optical examination, the method comprising applying an at least partially liquid, solid or gel-like sample to an optoelectronic chip according to claim 1 in such a way that the sample partially or completely surrounds the active region of the thin-film lightguide.

9. The method according to claim 8, wherein the sample contains at least one or a plurality of particle(s) that is/are capable of and/or designed to interact with a guided mode of the thin-film lightguide.

10. An optical system which is designed to be used with an optoelectronic chip according to claim 1, and designed to generate interference between a scattered light of a particle located in a sample space and a reference light generated by the scattering structure.

11. The optical system according to claim 10, which is further designed to detect the interference generated by means of a detector.

12. The optical system according to claim 11, wherein the detector is an array detector and/or the optical system is a microscope.

13. The optical system according to claim 10, which is designed to introduce light into a thin-film lightguide of an optoelectronic chip, such that a sample received in an active region of the thin-film lightguide can interact with the light.

14. A method of using an optoelectronic chip according to claim 1, comprising determining an antigen-antibody binding affinity, examining an antibody-antibody cross-linking and/or multi-site binding processes, to analyze protein-protein interactions, to estimate protein sizes, in the context of investigations on protein degradation and denaturation properties, and to optimize and characterize formulations.

15. The optoelectronic chip according to claim 1, wherein the scattering structure is formed regularly or irregularly and extends partially or completely over the active region and wherein the thin-film lightguide further has a structure for mode purification.

16. The optoelectronic chip according to claim 1, comprising at least two coupling regions; one for coupling in the mode guided in the thin-film lightguide and one for coupling out a part of the mode guided in the thin-film lightguide from the thin-film lightguide for monitoring an intensity of the guided mode and which contains an optically transparent thin-film heating element in addition to the thin-film lightguide.

17. An optoelectronic chip for receiving a sample for optical examination, having a carrier layer, a thin-film lightguide having an active region, in which the sample interacts with a guided mode of the thin-film lightguide, wherein at least one scattering structure is arranged in the active region, which scatters light guided in the thin-film lightguide, whereby a reference light field is produced, further comprising at least two coupling regions; one for coupling in the mode guided in the thin-film lightguide and one for coupling out a part of the mode guided in the thin-film lightguide from the thin-film lightguide for monitoring intensity of the guided mode.

18. The optoelectronic chip according to claim 17, wherein the coupling region for coupling out a part of the mode guided in the thin-film lightguide from the thin-film lightguide for monitoring the intensity of the guided mode runs at least in sections adjacent to a structure for mode purification.

19. The optoelectronic chip according to claim 18, wherein light is transferred from the thin-film lightguide into a reference lightguide for monitoring the intensity of the guided mode in the thin-film lightguide.

20. The optoelectronic chip according to claim 19, wherein light is transferred from the thin-film lightguide into a reference lightguide for monitoring the intensity of the guided mode in the thin-film lightguide by means of an evanescent coupling.

* * * * *